[19] United States Patent
Harrison et al.

[11] 3,965,723
[45] June 29, 1976

[54] WAX CONTENT MEASURING MEANS

[75] Inventors: Charles W. Harrison, Nederland; Theodore C. Mead, Port Arthur; Howard R. Moreland, Houston; Frank L. Barger, Port Arthur, all of Tex.

[73] Assignee: Texaco Inc., New York, N.Y.

[22] Filed: May 8, 1975

[21] Appl. No.: 575,759

[52] U.S. Cl. .................................. 73/53; 73/61 R
[51] Int. Cl.² .................. G01N 11/00; G01N 33/26
[58] Field of Search ....... 73/53, 61 R, 32 R, 61.1 R; 23/230 R, 230 HC; 235/151.35

[56] References Cited
UNITED STATES PATENTS 3,546,109  12/1970  Woodle ........................... 73/32 R X
3,557,609  1/1971  Woodle ................................ 73/53
3,720,096  3/1973  Woodle ................................ 73/53

Primary Examiner—Richard C. Queisser
Assistant Examiner—Joseph W. Roskos
Attorney, Agent, or Firm—T. H. Whaley; C. G. Ries; Ronald G. Gillespie

[57] ABSTRACT

A system measures and records the API gravity the viscosity and the sulfur content of waxy lubricating oil and provides corresponding signals. A computing circuit develops a signal corresponding to the wax content in accordance with the sensed parameter signals and an equation hereinafter disclosed. The wax content signal is recorded.

5 Claims, 1 Drawing Figure

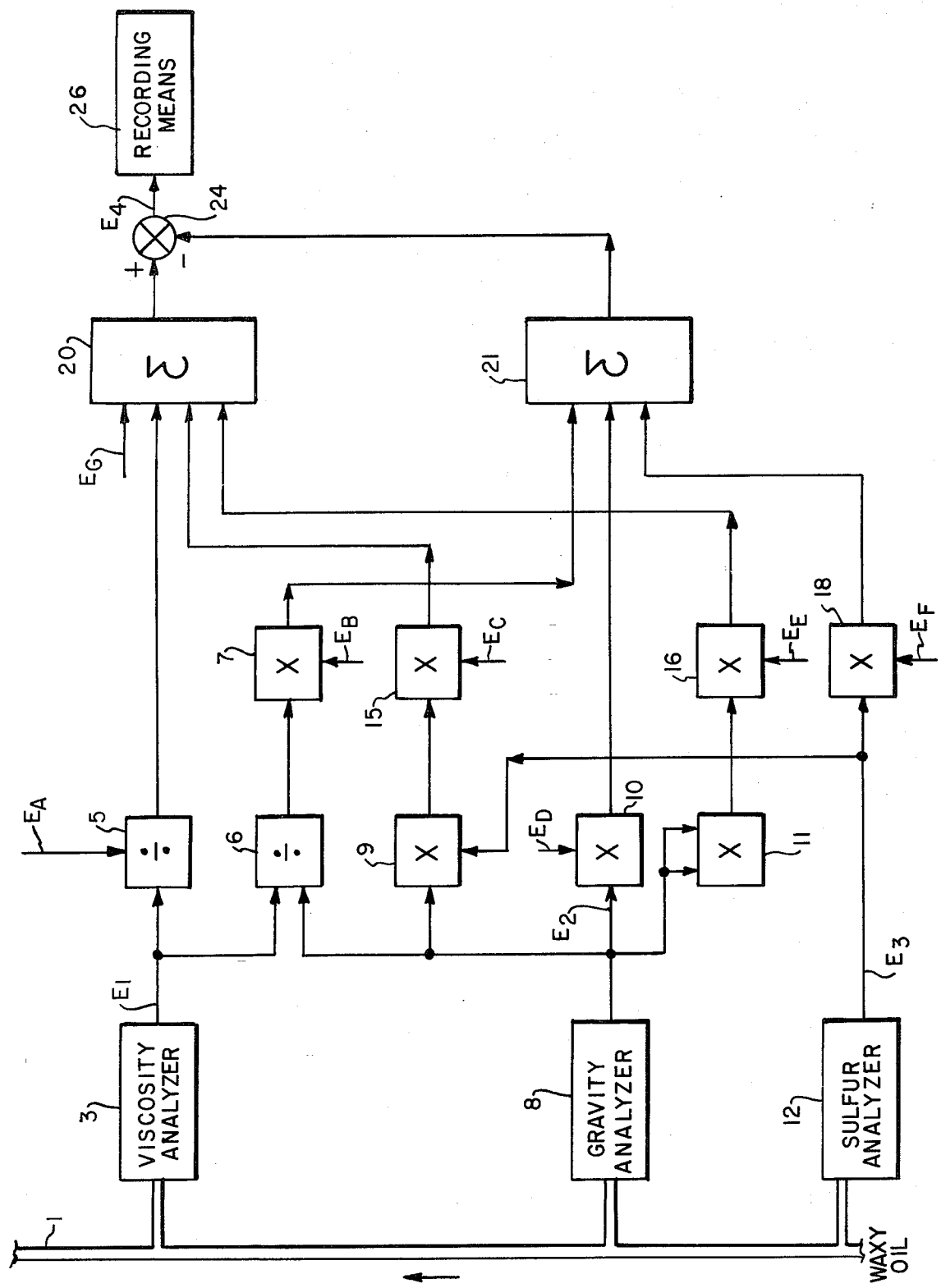

WAX CONTENT MEASURING MEANS

BACKGROUND OF THE INVENTION

Field of the Invention

The system of the present invention relates to measuring systems in general and, more particularly, to measuring systems in a refinery unit.

SUMMARY OF THE INVENTION

Apparatus measures the wax content of waxy oil. The apparatus includes sensors sensing the gravity, the viscosity and the sulfur content of the waxy oil and providing corresponding signals. A circuit provides a signal corresponding to the wax content of the waxy oil in accordance with the sensed parameter signals.

The object and advantages of the invention will appear more fully hereinafter, from a consideration of the detailed description which follows, taken together with the accompanying drawing wherein one embodiment is illustrated by way of example. It is to be expressly understood, however, that the drawing is for illustrative purposes only and is not to be construed as defining the limits of the invention.

DESCRIPTION OF THE DRAWING

The FIGURE shows a block diagram of a system, constructed in accordance with the present invention, for measuring the wax content of waxy oil.

DESCRIPTION OF THE INVENTION

The apparatus shown in the FIGURE determines the wax content by percent weight of wax in waxy oil flowing in a line 1. The wax content is determined in accordance with the following equation:

$$(1) \; W = C_1 - C_2 A + C_3 1/V - C_4 S + C_5 A^2 - C_6 A/V + C_7(A)(S)$$

where $C_1$ through $C_7$ are constants and the preferred embodiment, when the temperature of the waxy oil being analyzed by a viscosity analyzer is substantially 210°F, has values of 51.17, 4.3135, 182.83, 5.2388, 0.101, 6.6106 and 0.19609; W is the wax content in weight percent, A is the API gravity of the oil and V is the kinematic viscosity of the oil in centistokes.

A conventional type viscosity analyzer 3 samples the waxy oil in line 1 and provides a signal $E_1$ to dividers 5, 6. Divider 5 divides a direct current voltage $E_A$, corresponding to the constant $C_3$, by signal E, to provide a signal corresponding to the term $C_3 1/V$. Voltage $E_A$ is provided by a source of direct current voltages which is not shown for convenience. The direct current voltage source also provides direct current voltages $E_B$ through $E_G$.

A conventional type gravity analyzer 8 samples the waxy oil in line 1 and provides a signal $E_2$, corresponding to API gravity of the waxy oil in line 1, to divider 6 and to multipliers 9, 10 and 11. Divider 6 divides signal $E_2$ by signal $E_1$ to provide a signal, corresponding to the term A/V in the equation, to multiplier 7. Multiplier 7 multiplies the signal from divider 6 with voltage $E_B$, which corresponds to the constant $C_6$, to provide a signal corresponding to the term $C_6 A/V$.

A sulfur analyzer 12, which may be of conventional type, samples the waxy oil in line 1 and provides signal $E_3$ corresponding to the sulfur content of the waxy oil. Multiplier 9 multiplies signal $E_2$ with signal $E_3$ to provide a signal corresponding to the term AS in equation (1). A multiplier 15 multiplies the signal from multiplier 9 with voltage $E_C$, corresponding to the term $C_7$, to provide a signal corresponding to the term $C_7[A][S]$. Signal $E_2$ is multiplied with voltage $E_D$, corresponding to the term $C_2$, by multiplier 10, to provide a signal corresponding to the term $C_2 A$.

Multiplier 11 effectively squares the signal $E_2$ and provides a corresponding signal to another multiplier 16 where it is multiplied with voltage $E_E$ corresponding to the term $C_5$. Multiplier 16 provides a signal corresponding to the term $C_5 A^2$. A multiplier 18 multiplies signal $E_3$ with voltage $E_F$ to provide a signal corresponding to the term $C_4 S$.

All the positive terms in equation 1 are summed by summing means 20 and all the negative terms in equation 1 are summed by summing means 21. The sum signal provided by summing means 21 is then subtracted from the sum signal by subtracting means 24 to provide a signal $E_4$, corresponding to the term W, which is recorded by recording means 26. Summing means 20 sums the signals from divider 5 and multipliers 15 and 16 with voltages $E_G$ to provide its sum signal. Summing means 21 sums the signals from multipliers 7, 10, 18 to provide its sum signal.

The system of the present invention as heretofore described determines the wax content of waxy oil and provides a record thereof. The system senses the viscosity, the API gravity and the sulfur content of the oil and utilizes the sensed parameters to determine the wax content.

What is claimed is:

1. Means for determining the wax content of waxy oil, comprising means for sensing the viscosity of the waxy oil and providing a corresponding signal, means for sensing the gravity of the waxy oil and providing a signal corresponding thereto, means for sensing the sulfur content of the waxy oil and providing a signal representative thereof, means connected to all the sensing means for providing a signal corresponding to the wax content of the waxy oil in accordance with the sensed parameter signals.

2. Means as described in claim 1 in which the sensed gravity is the API gravity and the sensed viscosity is the kinematic viscosity.

3. Means as described in claim 2 in which the means for providing the signal corresponding to the wax content of the waxy oil includes means connected to the sensing means and providing a wax content signal in accordance with the sensed parameter signals and the following equation:

$$W = C_1 - C_2 A + C_3/V - C_4 S + C_5 A^2 - C_6 A/V + C_7(A)(S)$$

where W is the wax content of the oil, $C_1$ through $C_7$ are constants, A is the API gravity of the waxy oil, S is the sulfur content the waxy oil and V is the kinematic viscosity of the waxy oil.

4. Means as described in claim 3 in which the temperature of the waxy oil in the viscosity sensing means is substantially 210°F and the constants $C_1$ through $C_7$ have the following preferred values: 51.07, 4.3135, 182.83, 5.2388, 0.101, 6.6106 and 0.19609.

5. Means as described in claim 4 further comprising means receiving the wax content signal for recording the wax content signal.

* * * * *